United States Patent
Tarn et al.

(10) Patent No.: US 10,207,040 B2
(45) Date of Patent: Feb. 19, 2019

(54) ADJUSTING SOUND ON A MEDICAL DEVICE

(71) Applicant: Fresenius Medical Care Holdings, Inc., Waltham, MA (US)

(72) Inventors: Jeffrey Tarn, Walnut Creek, CA (US); Fei Wang, Concord, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 0 days.

(21) Appl. No.: 15/787,054

(22) Filed: Oct. 18, 2017

(65) Prior Publication Data
US 2018/0036466 A1   Feb. 8, 2018

Related U.S. Application Data

(63) Continuation of application No. 14/670,777, filed on Mar. 27, 2015, now Pat. No. 9,814,817.

(51) Int. Cl.
*G08B 21/00* (2006.01)
*A61M 1/14* (2006.01)
(Continued)

(52) U.S. Cl.
CPC ............ *A61M 1/14* (2013.01); *A61M 1/1601* (2014.02); *G08B 3/10* (2013.01); *G08B 29/18* (2013.01);
(Continued)

(58) Field of Classification Search
CPC .. A61M 1/14; A61M 1/1601; A61M 2205/18; A61M 2205/581;
(Continued)

(56) References Cited

U.S. PATENT DOCUMENTS

| 7,967,196 B1* | 6/2011 | Bierbaum | G06Q 20/127 235/375 |
| 8,117,699 B2* | 2/2012 | Richards | G10K 11/175 381/301 |

(Continued)

FOREIGN PATENT DOCUMENTS

| EP | 2422830 | 2/2012 |
| EP | 2787746 | 10/2014 |

OTHER PUBLICATIONS

Notification of Transmittal of the International Search Report and the Written Opinion of the International Searching Authority for corresponding PCT Application No. PCT/US2016/020888, dated May 20, 2016, 18 pages.

(Continued)

*Primary Examiner* — Tanmay Shah
(74) *Attorney, Agent, or Firm* — Fish & Richardson P.C.

(57) ABSTRACT

A dialysis machine comprising: a microphone; an alert module for producing an audible alert related to an operating condition of the dialysis machine; and a processing module configured for: receiving, from the microphone, information related to measured noise; determining, based on the information related to measured noise, an audible alert that will not be masked by the measured noise when the audible alert is produced by the alert module; and providing, to the alert module, instructions for producing the audible alert.

18 Claims, 7 Drawing Sheets

(51) Int. Cl.
  *G08B 3/10* (2006.01)
  *A61M 1/16* (2006.01)
  *G08B 29/18* (2006.01)
(52) U.S. Cl.
  CPC . *A61M 2205/18* (2013.01); *A61M 2205/3375* (2013.01); *A61M 2205/581* (2013.01); *A61M 2205/70* (2013.01)
(58) Field of Classification Search
  CPC ...... A61M 2205/70; A61M 2205/3375; G08B 29/18; G08B 3/10
  USPC .......................................................... 340/679
  See application file for complete search history.

(56) References Cited

U.S. PATENT DOCUMENTS

| | | | |
|---|---|---|---|
| 8,608,658 B2 | 12/2013 | Burbank et al. | |
| 8,718,797 B1 * | 5/2014 | Addepalli | H04W 4/046 700/17 |
| 2004/0100376 A1 | 5/2004 | Lye et al. | |
| 2006/0135907 A1 | 6/2006 | Remde et al. | |
| 2009/0088221 A1 | 4/2009 | Gilbert | |
| 2009/0113335 A1 | 4/2009 | Sandoe et al. | |
| 2009/0295591 A1 | 12/2009 | Bedingfield | |
| 2011/0185499 A1 | 8/2011 | Richards | |
| 2013/0277306 A1 * | 10/2013 | Chapman | A61M 1/28 210/644 |
| 2014/0107457 A1 * | 4/2014 | Raghunathan | A61B 5/0402 600/386 |
| 2014/0121845 A1 | 5/2014 | Mueller | |
| 2015/0025449 A1 | 1/2015 | Yuds et al. | |
| 2015/0054651 A1 | 2/2015 | Halbert et al. | |
| 2016/0283681 A1 | 9/2016 | Falck | |
| 2016/0346451 A1 | 12/2016 | Stonger et al. | |

OTHER PUBLICATIONS

U.S. Appl. No. 14/723,735, filed May 28, 2015, 36 pages.

* cited by examiner

ADJUSTING SOUND ON A MEDICAL DEVICE

CROSS REFERENCE TO RELATED APPLICATION

This application is a continuation and claims the priority of U.S. Ser. No. 14/670,777, filed Mar. 27, 2015, the entire contents of which are incorporated by reference herein.

TECHNICAL FIELD

This disclosure relates to adjusting sound on a medical device.

BACKGROUND

Dialysis is a treatment used to support a patient with insufficient renal function. Dialysis machines typically include audio output devices that can be used to alert nurses or doctors of events related to the dialysis treatment. For example, some dialysis machines output an audio tone that corresponds to an alarm condition.

SUMMARY

In one aspect, a dialysis machine includes a microphone. The dialysis machine also includes an alert module for producing an audible alert related to an operating condition of the dialysis machine. The dialysis machine also includes a processing module configured for receiving, from the microphone, information related to measured noise. The processing module is also configured for determining, based on the information related to measured noise, an audible alert that will not be masked by the measured noise when the audible alert is produced by the alert module. The processing module is also configured for providing, to the alert module, instructions for producing the audible alert.

Implementations can include one or more of the following features.

In some implementations, the processing module is configured to identify a type of the measured noise.

In some implementations, the measured noise is ambient noise.

In some implementations, the measured noise is a second audible alert.

In some implementations, the second audible alert is related to an operating condition of a second dialysis machine.

In some implementations, the information related to the ambient noise includes a measurement of a volume of the ambient noise.

In some implementations, the instructions cause the alert module to produce an audible alert that is louder than the volume of the ambient noise.

In some implementations, the information related to the second audible alert includes a measurement of a timing of the second audible alert.

In some implementations, the instructions cause the alert module to produce an audible alert that has a timing that is out of phase with the timing of the second audible alert.

In some implementations, the information related to the second audible alert includes a measurement of a frequency of the second audible alert.

In some implementations, the instructions cause the alert module to produce an audible alert of a frequency different from the frequency of the second audible alert.

In some implementations, the audible alert has a frequency that is within a predefined range.

In some implementations, the instructions for producing the audible alert are based at least in part on the type of the measured noise.

In some implementations, the instructions for producing the audible alert are based at least in part on the priority of the audible alert.

In some implementations, the instructions cause the alert module to produce an audible alert that is louder than lower-priority audible alerts that are measured by the microphone.

In another aspect, a method includes receiving, from a microphone of a dialysis machine, information related to measured noise. The method also includes determining, based on the information related to measured noise, an audible alert related to an operating condition of the dialysis machine. The audible alert is determined such that the audible alert will not be masked by the measured noise when the audible alert is produced by an alert module of the dialysis machine. The method also includes providing, to the alert module, instructions for producing the audible alert.

In another aspect, a system includes a dialysis machine. The dialysis machine includes a microphone. The dialysis machine also includes an alert module for producing an audible alert related to an operating condition of the dialysis machine. The dialysis machine also includes a processing module configured for receiving, from the microphone, information related to measured noise. The processing module is also configured for determining, based on the information related to measured noise, an audible alert that will not be masked by the measured noise when the audible alert is produced by the alert module. The processing module is also configured for providing, to the alert module, instructions for producing the audible alert.

In another aspect, a computer-readable storage device storing a computer program includes instructions for causing a computer to receive, from a microphone of the dialysis machine, information related to measured noise. The computer program also includes instructions for causing the computer to determine, based on the information related to measured noise, an audible alert related to an operating condition of the dialysis machine. The audible alert is determined such that the audible alert will not be masked by the measured noise when the audible alert is produced by an alert module of the dialysis machine. The computer program also includes instructions for causing the computer to provide, to the alert module, instructions for producing the audible alert.

Implementations can include one or more of the following advantages.

In some implementations, the volume of the audible alert can be adjusted such that it is not unnecessarily loud for the particular environmental noise conditions.

In some implementations, the volume of the audible alert can be adjusted such that it can be heard over environmental noise.

In some implementations, the timing of the audible alert can be adjusted such that it is out of phase with one or more other audible alerts (e.g., from other dialysis machines).

In some implementations, the frequency (e.g., pitch) of the audible alert can be adjusted such that the audible alert is not masked by one or more other audible alerts (e.g., from other dialysis machines).

Other aspects, features, and advantages of the invention will be apparent from the description and drawings, and from the claims.

DETAILED DESCRIPTION

Dialysis machines typically use audible sounds as alerts for various operating conditions. For example, when a dialysis machine detects a condition that requires the attention of a human being, the dialysis machine may play a sound than an operator may recognize as associated with either the specific condition or error conditions in general. In a noisy environment, these audible alerts may be drowned out by ambient noise. Similarly, if multiple dialysis machines are in the same location, an audible alert from one dialysis machine may be masked by audible alerts from other dialysis machines.

A dialysis machine can be configured to adapt its audio output based on the audio characteristics of its environment. A particular dialysis machine can include a microphone for measuring ambient noise and audible alerts from other dialysis machines. A processing module can analyze the sound measurements to determine whether the ambient noise and the audible alerts from other dialysis machines are interfering with the audible alerts of the particular dialysis machine. If appropriate, the dialysis machine can make adjustments to its audible alert so that the audible alert can be perceived over the ambient noise and the audible alerts from other dialysis machines.

One technique that a dialysis machine can use is the adjustment of its output volume. In some examples, if the processing module determines that ambient noise is downing out the dialysis machine's audible alerts, the volume of the audible alerts can be automatically increased. Similarly, if the processing module determines that there is very little ambient noise, the volume of the audible alerts can be automatically decreased.

Another technique that a dialysis machine can use is the adjustment of the timing of its audio output signal. In some examples, if the processing module determines that audible alerts from other dialysis machines are masking the particular dialysis machine's audible alert, the timing of the particular dialysis machine's audible alert can be adjusted. For example, assuming that the audible alerts are made up of repetitive beeps, the audible alert of the particular dialysis machine can be adjusted such that the beeps are out of phase with the beeps of the audible alerts from the other dialysis machines.

Yet another technique that a dialysis machine can use is the adjustment of the frequency of its audio output signal. In some situations, one sound may mask another sound if the frequencies of the two sounds interfere with each another. If the processing module determines that frequencies of audible alerts from other dialysis machines are causing the particular dialysis machine's audible alert to be masked, the frequency of the particular dialysis machine's audible alert can be adjusted.

Figure 1:
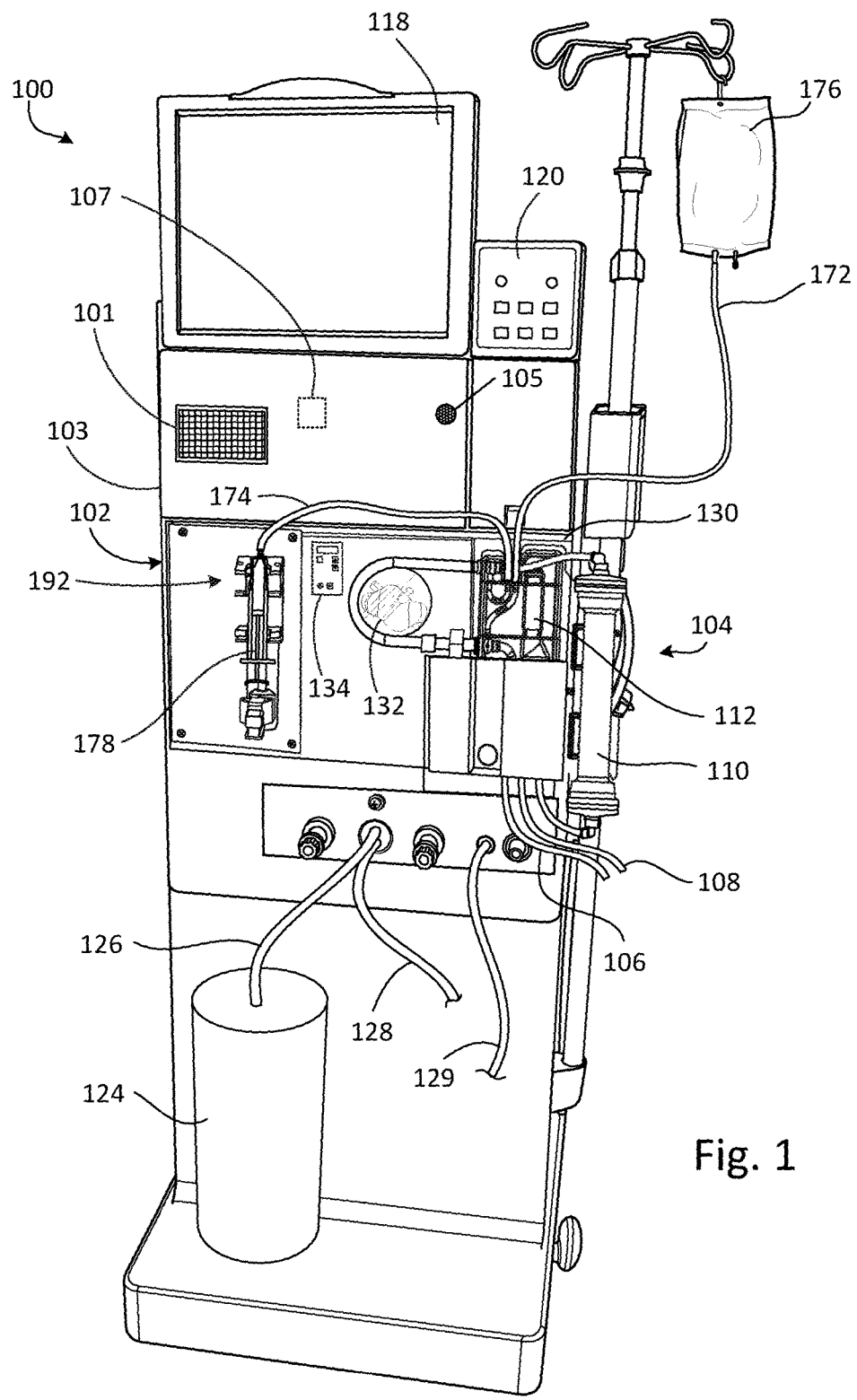
FIG. 1 is a front perspective view of a hemodialysis system, including a speaker and a microphone.

FIG. 1 shows a hemodialysis system 100 configured to adapt its audio output based on audio conditions of its environment. The hemodialysis system 100 includes a hemodialysis machine 102 to which a disposable blood component set 104 that forms a blood circuit is connected. During hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing 103 of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

One of the components of the blood component set 104 is an air release device 112. The air release device 112 includes a self-sealing vent assembly that allows air to pass therethrough while inhibiting (e.g., preventing) liquid from passing therethrough. As a result, if blood passing through the blood circuit during treatment contains air, the air will be vented to atmosphere as the blood passes through the air release device 112.

As shown in FIG. 1, a dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 attached to the front of the hemodialysis machine 102. The module 130 includes a blood pump 132 capable of driving blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130. As described in greater detail below, this arrangement facilitates control of the flow of blood through the blood circuit and monitoring of the blood flowing through the blood circuit.

The blood pump 132 can be controlled by a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes an alert module such as a speaker 101, an audio input device such as a microphone 105, a touch screen 118 and a control panel 120. The touch screen 118 and the control panel 120 allow the operator to input various different treatment parameters to the hemodialysis machine 102 and to otherwise control the hemodialysis machine 102. In addition, the touch screen 118 serves as a display to convey information to the operator of the hemodialysis system 100. In the example shown in FIG. 1, the speaker 101 and the microphone 105 are positioned below the touch screen 118 and together function to provide customized audio signals (e.g., as alerts) to the operator of the system 100. Thus, the hemodialysis machine 102 is capable of providing both visual alerts via the touch screen 118 and customized audio alerts via the speaker 101 to the operator of the system 100 during use.

The hemodialysis machine 102 includes a processing module 107 that resides inside the machine and which is connected to the touch screen 118, the control panel 120, the speaker 101, and the microphone 105. The processing module 107 is configured to receive data that is input via the touch screen 118 and the control panel 120 and control the hemodialysis machine 102 based on the received data. For example, the processing module 107 can adjust the operating parameters of the hemodialysis machine 102. The processing module 107 is also configured to provide instructions to the speaker 101 based on the operating parameters of the hemodialysis machine 102 and information related to measured noise. The information related to measured noise can be in the form of audio data received from the microphone 105. In some examples, if the processing module 107 determines that a condition exists that requires that an alert be sound, the processing module 107 can provide instructions to the speaker 101 that cause the speaker 101 to sound an alert. Further, if the audio data received from the microphone 105 indicate that the alert may not be effectively heard by an individual in proximity, the processing module 107 can cause the speaker 101 to adjust the alert accordingly such that the audible alert will not be masked by the measured noise.

Figure 2:
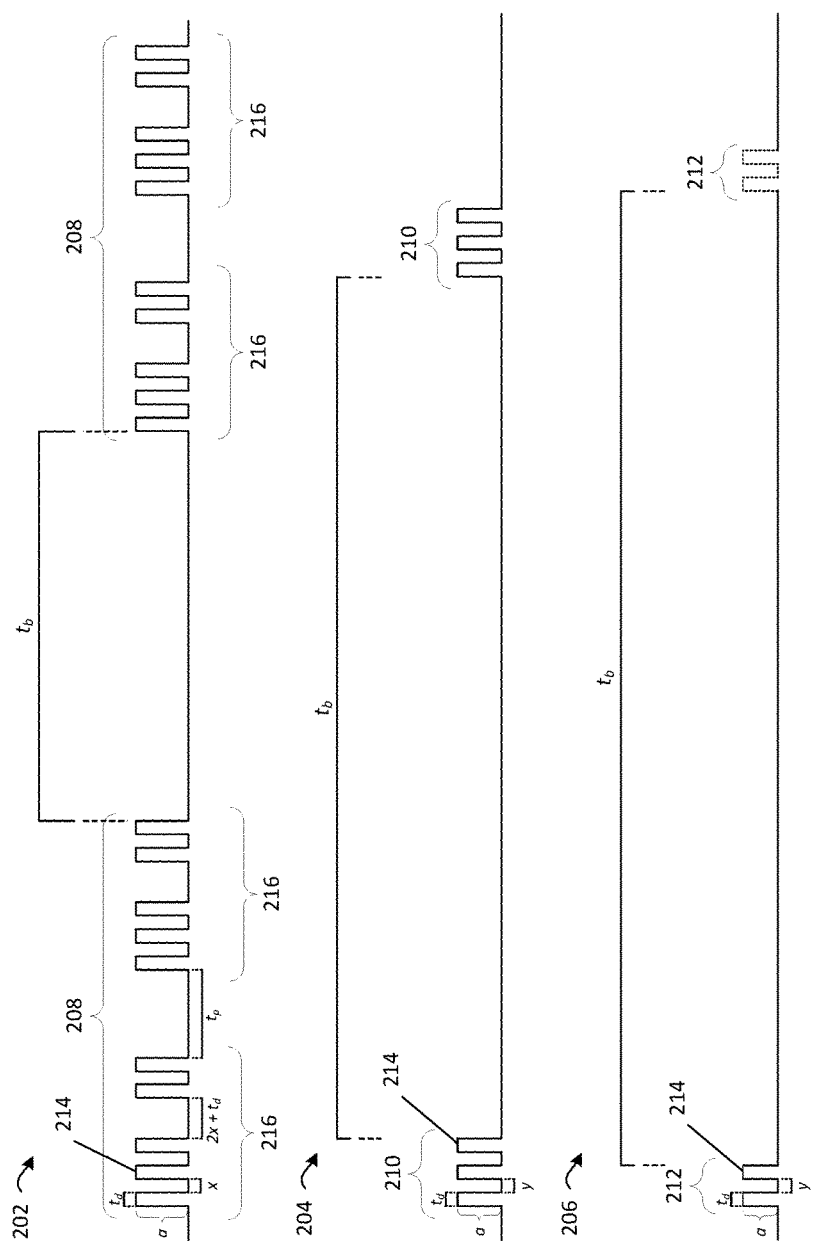
FIG. 2 shows examples of alarm signals having different priorities.

Alerts can take on different forms depending on the triggering condition. In some examples, alerts can be split up into multiple groups. FIG. 2 shows an example of three alarm signals having three different priorities: a high priority alarm signal 202, a medium priority alarm signal 204, and a low priority alarm signal 206. The alarm signals can be related to various health conditions of the patient, such as cardiovascular conditions, oxygenation conditions, ventilation conditions, temperature conditions, drug delivery conditions, fluid delivery conditions, or artificial perfusion conditions. The alarm signals can also be related to various conditions or states of the hemodialysis machine 102. For example, an alarm signal may indicate that the hemodialysis machine 102 is in a "general" or "advisory" state. In some examples, an alarm signal may indicate that the hemodialysis machine 102 is in a power-up, a power-down, or a power failure state.

Each alarm signal 202, 204, 206 can include one or more bursts. The high priority alarm signal 202 includes at least two bursts 208. The medium priority alarm signal 204 includes at least two bursts 210. The low priority alarm signal 206 includes at least one burst 212. A second burst 212 is optional. In some examples, low priority alarm signals only include a single burst.

Each burst 208, 210, 212 includes one or more notes 214 (sometimes referred to as pulses), each of which has an effective pulse duration $t_d$. The $t_d$ can have a value of 75 ms to 200 ms for the high priority alarm signal 202 and a value of 125 ms to 250 ms for the medium priority 204 and low priority 206 alarm signals.

Each burst 208$a$, 208$b$ of the high priority alarm signal 202 includes a pattern of five notes 216 played twice, totaling ten notes in each burst. Each burst of the medium priority alarm signal 204 includes a pattern of three notes. Each burst (if there is more than one burst) of the low priority alarm signal 206 includes a pattern of two notes. In some examples, low priority alarm signals only include a single note in each burst.

Bursts 208, 210, 212 of the alarm signals can be separated by a period of time, the length of which can depend on the priority of the alarm. For example, the interburst interval ($t_b$) for the high priority alarm signal 202 can be 2.5 to 15 seconds, the $t_b$ for the medium priority alarm signal 204 can be 2.5 to 30 seconds, and the $t_b$ for the low priority alarm signal 206 can be greater than 15 seconds. In some examples, low priority alarm signals do not repeat (e.g., they only sound once), so there is no $t_b$.

The notes 214 of the alarms are separated by a period of time, the length of which can depend on the priority of the alarm. Referring to the high priority alarm signal 202, the first and second notes, the second and third notes, and the fourth and fifth notes of each five-note pattern 216 are separated by a period of time x. The period of time x can have a value between 50 ms and 125 ms. The third and fourth notes of each five-note pattern 216 are separated by a period of time $2x+t_d$. Successive five-note patterns 216 are separated by a period of time $t_p$. The period of time $t_p$ can have a value of 0.35 s to 1.3 s. Referring to the medium priority alarm signal 204, the first and second notes and the second and third notes of each burst 210 are separated by a period of time y. The period of time y can have a value between 125 ms and 250 ms. Referring to the low priority alarm signal 206, the first and second notes (if there is a second note) of each burst 212 are separated by the period of time y.

Irrespective of the priority of an alarm signal, the pitch of an alarm signal can indicate the condition or event that triggered the alarm. In this way, two alarm signals can be distinguished based on the pitch of the signal. For example, a general alarm may have a fixed pitch (e.g., each note/pulse of the alarm has the same frequency of vibration), while an oxygen alarm may have falling pitches (e.g., each note/pulse of the alarm has a frequency of vibration that is less than the preceding note). The pitch may be expressed as a musical tone that has a relative position on a musical scale. In an example of a medium priority general alarm signal, the pitch of the notes may be three successive "C" notes, while in an example of a medium priority oxygen alarm, the pitch may be "C" for the first note, "B" for the second note, and "A" for the third note. Additional notes may be included in the alarm signal depending on the priority of the alarm. In an example of a high priority general alarm signal, the pitch of the notes may be five successive "C" notes, while in an example of a high priority oxygen alarm, the pitch may be "C" for the first note, "B" for the second note, "A" for the third note, "G" for the fourth note, and "F" for the fifth note. In this example, the "G" note and the "F" note are one octave lower than the octave of the first three notes, thereby resulting in five notes with falling pitches.

In addition to the timing and pitch, the amplitude (sometimes referred to informally as volume) of the notes in an alarm signal can be used to convey information to the operator of the hemodialysis system 100. The amplitude of the notes of an alarm signal (signified by the variable "a" in FIG. 2) can depend on the priority of the particular alarm signal. For example, still referring to FIG. 2, the notes 214 of the high priority alarm signal 202 have a larger amplitude than the amplitude of the notes 214 of the medium priority alarm signal 204, and the notes 214 of the medium priority alarm signal 204 have a larger amplitude than the amplitude of the notes 214 of the low priority alarm signal 206. As such, the high priority alarm signal 202 is louder than the other two alarm signals 204, 206 and is more likely to be heard.

The values for the variables a, x, y, $t_b$, $t_d$, and $t_p$ may be mandated, e.g., by guidelines created and/or published by a standards organization. In some examples, the values for the variables are mandated by the International Organization for Standardization (ISO) and/or the International Electrotechnical Commission (IEC). In some examples, the values for the variables conform to IEC 60601-1-8 standards.

Figure 3A:
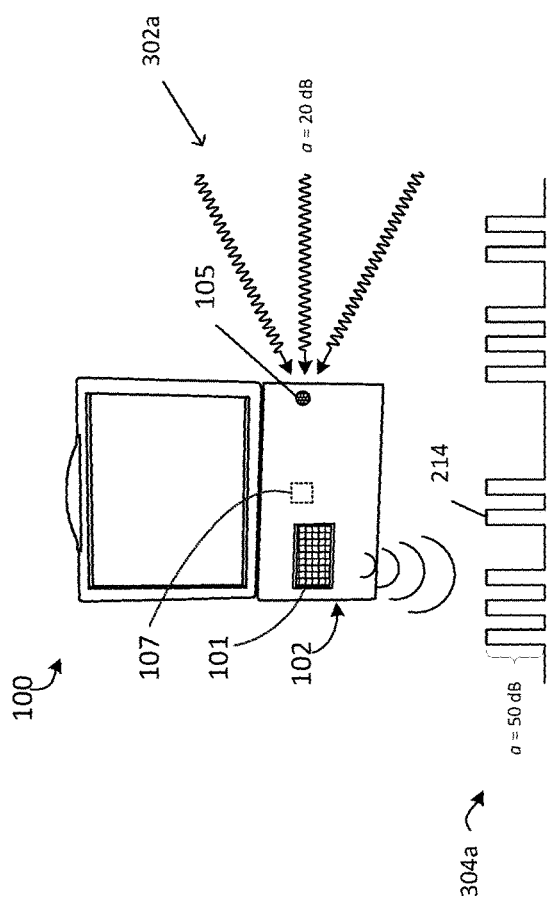
FIG. 3a shows an example of a hemodialysis system that is in a relatively quiet environment.

In some implementations, it may be desirable to adjust characteristics of an alarm signal for a number of reasons. For example, the characteristics of an alarm signal can be adjusted based on the amount of ambient noise measured in a room. FIG. 3a shows an example of a hemodialysis system 100 that is in a relatively quiet environment. The hemodialysis system 100 may be, for example, in a quiet wing of a hospital or in a room occupied by only the single patient. An operator of the hemodialysis machine 102 may prefer that the volume of an alarm signal 304a is reduced so that the patient is not startled when an alarm is activated. The operator need not manually adjust the volume of the alarm signal 304a that will be emitted by the speaker 101. Instead, the hemodialysis machine 102 is configured to measure ambient noise 302a and automatically adjust the volume of the alarm signal accordingly. The microphone 105 measures ambient noise 302a and provides audio data to the processing module 107. In this example, the ambient noise 302a is relatively quiet (e.g., the amplitude of the ambient noise 302a is relatively small, 20 dB). The processing module 107 analyzes the audio data and determines an appropriate volume for the alarm signal 304a. In this example, because the ambient noise 302a is relatively quiet, the processing module 107 determines that an alarm signal 304a having an amplitude of 50 dB is sufficient and appropriate. The processing module 107 instructs the speaker 101 to sound the alarm signal 304a at the computed amplitude of 50 dB. The processing module 107 may use an algorithm to determine the appropriate amplitude for the alarm signal 304a. In some implementations, the appropriate amplitude for the alarm signal 304a is based at least in part on guidelines and/or standards created or enforced by a regulatory body.

Figure 3B:
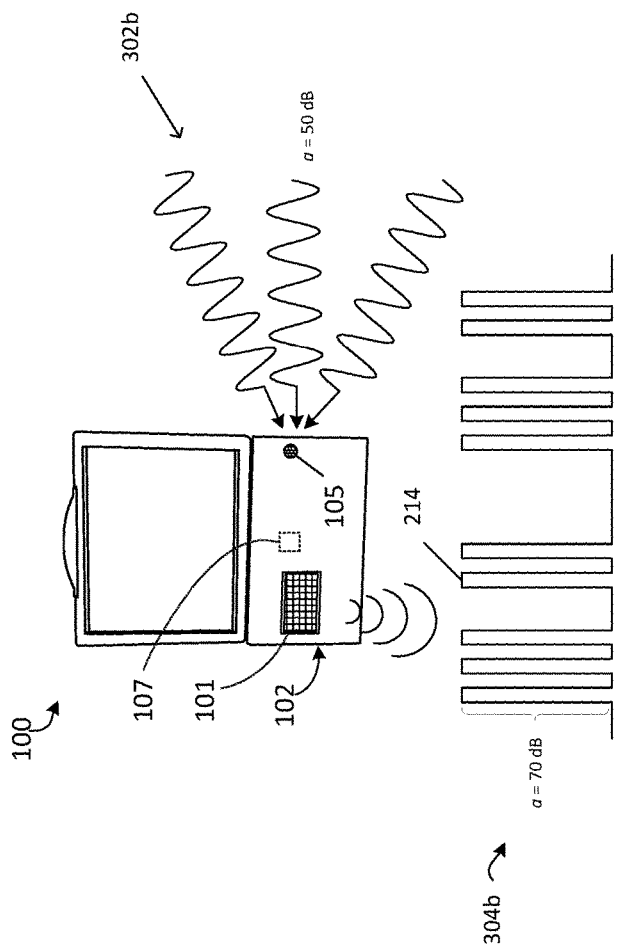
FIG. 3b shows an example of a hemodialysis system that is in a relatively noisy environment.

FIG. 3b shows an example of a hemodialysis system 100 that is in a relatively noisy environment. The hemodialysis system 100 may be, for example, in a communal area of a hospital or in a room occupied by multiple patients (e.g., in a dialysis clinic). The operator of the hemodialysis machine 102 may want the volume of an alarm signal 304b to be increased so that the operator can hear the alarm over ambient noise 302b. The microphone 105 measures the ambient noise 302b and provides audio data to the processing module 107. In this example, the ambient noise 302b is relatively loud (e.g., the amplitude of the ambient noise 302b is relatively large, 50 dB). The processing module 107 analyzes the audio data and determines an appropriate volume for the alarm signal 304b. In this example, because the ambient noise 302b is relatively loud, the processing module 107 determines that an alarm signal 304b having an amplitude of 70 dB is sufficient and appropriate. The processing module 107 instructs the speaker 101 to sound the alarm signal 304b at the computed amplitude of 70 dB.

Other characteristics of an alarm signal can also be adjusted instead of or in addition to the volume. In some implementations, multiple hemodialysis systems are located in relatively close proximity to each other. If two or more hemodialysis machines are emitting alarm signals at the same time, one or more of the alarm signals may be masked (e.g., drowned out) by the other.

Figure 4:
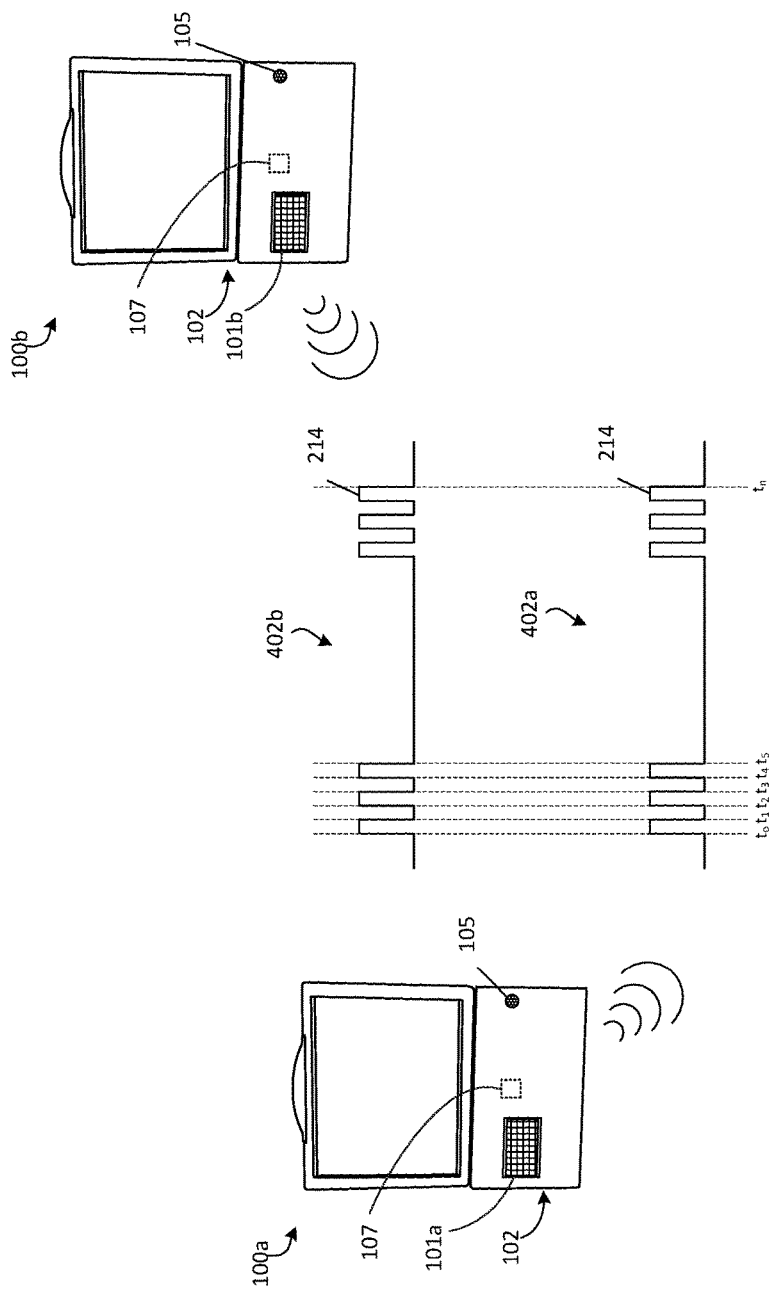
FIG. 4 shows an example of hemodialysis systems that are within audible range of each other.

FIG. 4 shows an example of two hemodialysis systems 100a, 100b that are within audible range of each other. The speakers 101a, 101b are emitting respective alarm signals 402a, 402b. In this example, the alarm signals 402a, 402b are masking each other. The notes 214 of the alarm signal 402a from one hemodialysis system 100a sound at the same times ($t_o$, $t_1$, . . . $t_n$) as the notes 214 of the alarm signal 402b from the other hemodialysis system 100b. As such, an operator of the hemodialysis systems 100a, 100b may be unable to discern between the two alarm signals 402a, 402b. One technique that can be used to remedy this issue is to adjust the volume of one of the alarm signals in a similar manner as described above with reference to FIG. 3b. However, doing so would simply allow the adjusted alarm signal (e.g., 402a) to be heard over the unadjusted alarm signal (e.g., 402b) while further masking the unadjusted alarm signal. Instead, the timings of one or both of the alarm signals 402a, 402b can be adjusted so that the two alarm signals 402a, 402b are out of sync, thus allowing a listener to better hear both alarm signals simultaneously.

Figure 5:
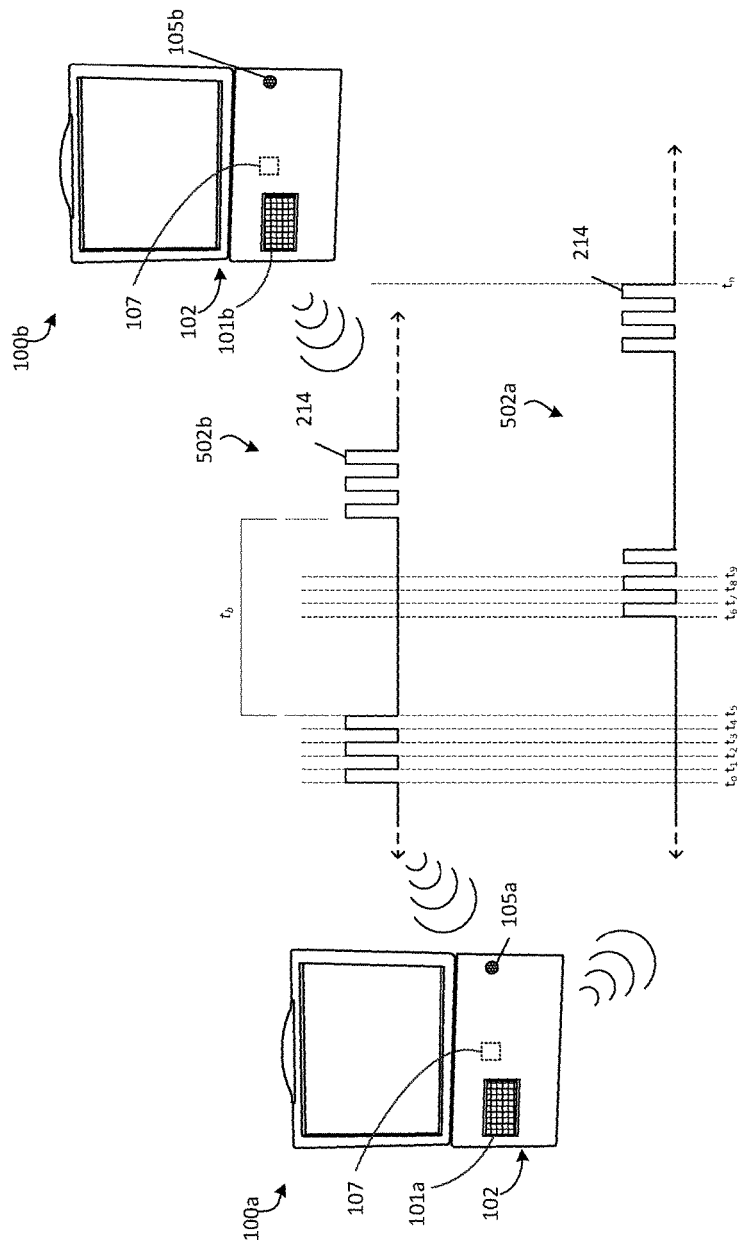
FIG. 5 shows an example of a timing-adjusted alarm signal.

FIG. 5 shows an example of an alarm signal 502a that has note timings defined such that the alarm signal 502a is not masked by a different alarm signal 502b. The speaker 101b of one of the hemodialysis systems 100b plays an alarm signal 502b. The microphone 105a of the other hemodialysis system 100a measures the alarm signal 502b and provides audio data to the processing module 107. The processing module 107 also determines that an alarm condition exists in the hemodialysis system 100a, and thus an alarm signal should be emitted by the speaker 101a. The processing module 107 analyzes the audio data and determines appropriate timings for the alarm signal 502a. In this example, the processing module 107 determines that the alarm signal 502b from the other hemodialysis system 100b has a period of silence between bursts that is defined by the interburst interval ($t_b$). The processing module 107 determines that the bursts of the alarm signal 502a from the hemodialysis system 100a should occur during the $t_b$ of the alarm signal 502b from the other hemodialysis system 100b, and the processing module 107 instructs the speaker 101a to sound the bursts of the alarm signal 502a at the determined time windows. In this way, both alarm signals 502a, 502b can be better discerned by the operator of the hemodialysis systems 100a, 100b.

Figure 6:
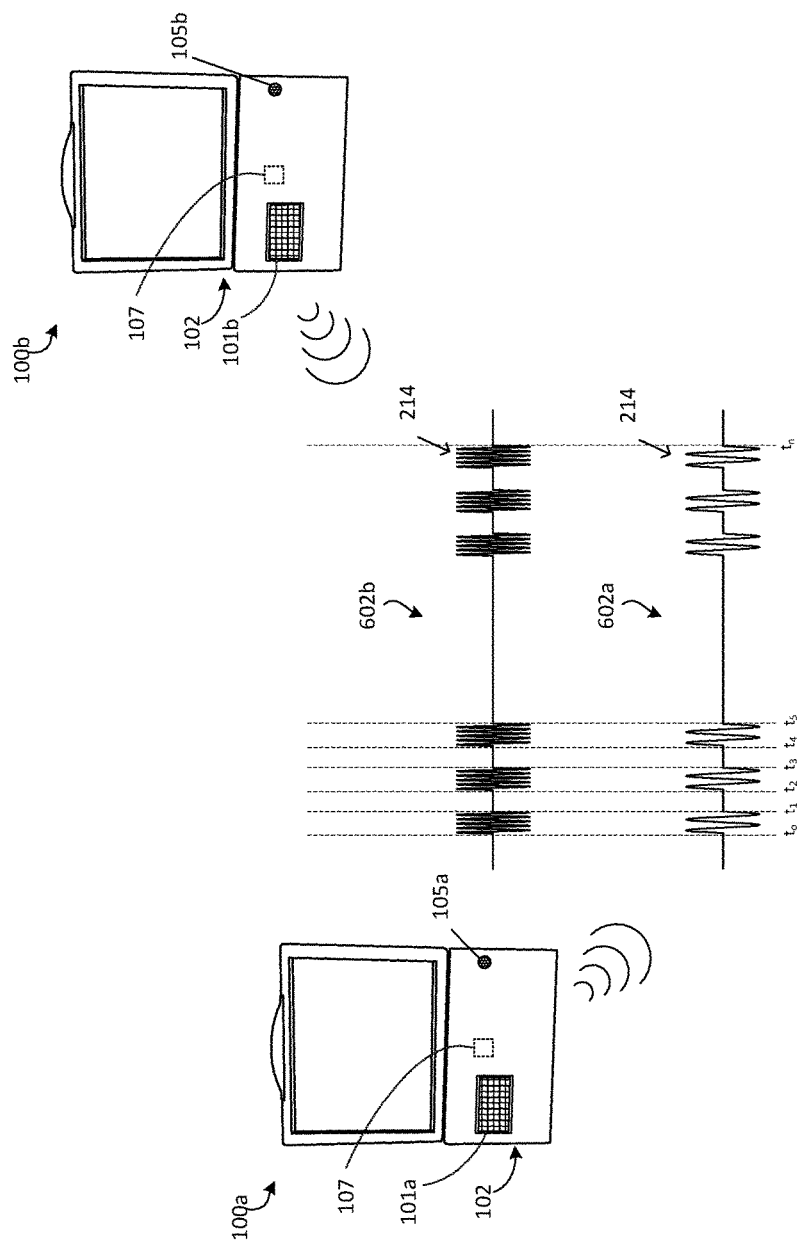
FIG. 6 shows an example of a frequency-adjusted alarm signal.

In some implementations, if two or more hemodialysis machines are emitting alarm signals at the same time, the frequencies (sometimes informally referred to as pitch) of one or both of the alarm signals can be adjusted so that the operator can better discern the two alarm signals. FIG. 6 shows an example of an alarm signal 602a that has had its frequency defined such that the alarm signal 602a is not masked by a different alarm signal 602b. In this example, the alarm signals 602a, 602b are represented according to their relative frequencies as indicated by the waveform of each note 214. The speaker 101b of one of the hemodialysis systems 100b plays an alarm signal 602b. The microphone 105a of the other hemodialysis system 100a measures the alarm signal 602b and provides audio data to the processing module 107. The processing module 107 also determines that an alarm condition exists in the hemodialysis system 100a, and thus an alarm signal needs to be emitted by the speaker 101a. The processing module 107 analyzes the audio data and determines an appropriate frequency for the alarm signal 502a. In this example, the processing module 107 determines that the alarm signal 502b from the other hemodialysis system 100b has a frequency $f_b$. The processing module 107 determines that an alarm signal 602a with a frequency of $f_a$ would not be masked by the alarm signal 602b from the other hemodialysis system 100b. The processing module 107 instructs the speaker 101a to sound an alarm signal 602a with the defined frequency $f_a$. In this way, both alarm signals 602a, 602b can be discerned by the operator of the hemodialysis systems 100a, 100b.

As described above, the pitch of an alarm signal can indicate the condition or event that triggered the alarm. In this way, the musical tones of the notes of an alarm signal can convey information to the operator. As such, in some implementations, the processing module 107 may consider a type of an alarm signal when defining an appropriate frequency to prevent masking. For example, a relatively important alarm (e.g., an alarm indicating a potentially lethal cardiovascular condition of the dialysis patient) may include one or more notes having high-pitched frequencies that are designed to be audibly distinctive. The processing module 107 may be configured to only adjust the frequency of the cardiovascular alarm to a frequency that resides within a predefined range to prevent the cardiovascular alarm from losing its distinctive pitch. In some implementations, the processing module 107 may be configured to instruct another hemodialysis system (e.g., a hemodialysis system that is emitting a masking alarm signal) to adjust its own alarm signal. In this way, the alarm signal that ends up being adjusted may be determined according to the relative importance of the alarm signals.

In some implementations, the processing module 107 can be configured to identify generally what type of noise the microphone 105 is measuring. For example, the processing module 107 can identify whether the measured noise is ambient noise or an alarm signal, e.g., by comparing the measured noise to stored profiles representing the audio of known alarm signals. The type of the measured noise may impact the manner in which the processing module 107 adjusts the alarm signals of the hemodialysis machine 100. For example, if the processing module 107 identifies the measured noise as environmental noise, the processing module 107 may adjust the volume of the emitted alarm. On the other hand, if the processing module 107 identifies the measured noise as an alarm signal, the processing module 107 may adjust the timing or the frequency of the emitted alarm.

A method of using the hemodialysis system 100 to administer a dialysis treatment to a patient will now be described.

Before treatment begins, an operator enters information into the hemodialysis machine 102 via the touch screen 118 and/or the control panel 120. The operator typically enters patient parameters and medical treatment information, and the hemodialysis machine 102 determines appropriate operating parameters for the patient's treatment. Once the patient parameters and the medical treatment information are entered, the operator prepares the patient for dialysis treatment. Referring back to FIG. 1, the arterial and venous patient lines 106, 108 are connected to the patient, and hemodialysis is initiated. During hemodialysis, blood is circulated through the blood circuit (i.e., the various blood lines and blood components, including the dialyzer 110, of the blood component set 104). At the same time, dialysate is circulated through the dialysate circuit (i.e., the various dialysate lines and dialysate components, including the dialyzer 110).

During treatment, one or more alarm conditions may arise. For example, the hemodialysis machine 102 may detect a problem with the power source. The processing module 107 may determine that a power failure alarm signal should be sounded. Before sounding the power failure alarm signal, the processing module 107 may receive audio data from the microphone 105.

In one example, the audio data may indicate that there is minimal environmental noise detected, and the processing module 107 can instruct the speaker 101 of the hemodialysis machine 102 to sound the power failure alarm signal at an appropriate volume (e.g., a relatively low volume that can be easily heard by the operator).

In another example, the audio data may indicate that significant environmental noise exists. The environmental noise may include general noise that are caused by people talking, HVAC systems running, etc. The processing module 107 can instruct the speaker 101 of the hemodialysis machine 102 to sound the power failure alarm signal at an appropriate volume (e.g., a volume that can be heard by the operator over the environmental noise).

In another example, the audio data may indicate that an alarm signal from another hemodialysis system is within audible range of the microphone. The processing module 107 can instruct the speaker 101 of the hemodialysis machine 102 to sound bursts of the power failure alarm signal at particular timings such that the bursts occur during periods of silence of the other alarm signal. Alternatively, the processing module 107 can instruct the speaker 101 of the hemodialysis machine 102 to sound the power failure alarm signal with an adjusted frequency such that the power failure alarm signal can be discerned by the operator over the other alarm signal.

While certain implementations have been described, other implementations are possible.

While we have described various variables that define aspects of the alarm signal which may be mandated by guidelines created and/or published by a standards organization, the alarm signal may be defined in other ways. In some implementations, the alarm signal is custom designed (e.g., by the manufacturer of the dialysis machine). In some implementations, one or more of the variables (e.g., a, x, y, $t_b$, $t_d$, $t_p$) can have values different than those described above.

While we have described the alarm being adjusted and emitted by a hemodialysis machine, the alarm could alternatively be adjusted and emitted by other types of medical treatment systems. Examples of other medical treatment systems that may employ the techniques described herein include hemofiltration systems, hemodiafiltration systems, apheresis systems, cardiopulmonary bypass systems, and peritoneal dialysis systems.

Implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor (e.g., processing module), a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations have been described. Nevertheless, it will be understood that various modifications may be made without departing from the spirit and scope of the invention. Accordingly, other implementations are within the scope of the following claims.

What is claimed is:

1. A dialysis machine comprising:
    a microphone;
    an alert module for producing an audible alert related to an operating condition of the dialysis machine; and
    a processing module configured for:
        receiving, from the microphone, information related to measured noise;
        identifying a type of the measured noise;
        determining, based on the information related to the measured noise and the identified type of the measured noise, an audible alert that will not be masked by the measured noise when the audible alert is produced by the alert module; and
        providing, to the alert module, instructions for producing the audible alert.

2. The dialysis machine of claim 1, wherein the measured noise is ambient noise.

3. The dialysis machine of claim 2, wherein the information related to the ambient noise includes a measurement of a volume of the ambient noise.

4. The dialysis machine of claim 3, wherein the instructions cause the alert module to produce an audible alert that is louder than the volume of the ambient noise.

5. The dialysis machine of claim 1, wherein the measured noise is a second audible alert.

6. The dialysis machine of claim 5, wherein the second audible alert is related to an operating condition of a second dialysis machine.

7. The dialysis machine of claim 5, wherein the information related to the second audible alert includes a measurement of a timing of the second audible alert.

8. The dialysis machine of claim 7, wherein the instructions cause the alert module to produce an audible alert that has a timing that is out of phase with the timing of the second audible alert.

9. The dialysis machine of claim 5, wherein the information related to the second audible alert includes a measurement of a frequency of the second audible alert.

10. The dialysis machine of claim 9, wherein the instructions cause the alert module to produce an audible alert of a frequency different from the frequency of the second audible alert.

11. The dialysis machine of claim 10, wherein the audible alert has a frequency that is within a predefined range.

12. The dialysis machine of claim 1, wherein the instructions for producing the audible alert are based at least in part on the priority of the audible alert.

13. The dialysis machine of claim 12, wherein the instructions cause the alert module to produce an audible alert that is louder than lower-priority audible alerts that are measured by the microphone.

14. The dialysis machine of claim 1, wherein the instructions cause the alert module to produce an audible alert having a pitch indicative of a condition or event that corresponds to the audible alert.

15. The dialysis machine of claim 1, wherein the processing module is configured for instructing a second dialysis system emitting the measured noise to adjust one or more characteristics of the measured noise.

16. A method comprising:
   receiving, from a microphone of a dialysis machine, information related to measured noise;
   identifying a type of the measured noise;
   determining, based on the information related to the measured noise and the identified type of the measured noise, an audible alert related to an operating condition of the dialysis machine, the audible alert determined such that the audible alert will not be masked by the measured noise when the audible alert is produced by an alert module of the dialysis machine; and
   providing, to the alert module, instructions for producing the audible alert.

17. A system comprising:
   a dialysis machine comprising:
      a microphone;
      an alert module for producing an audible alert related to an operating condition of the dialysis machine; and
      a processing module configured for:
         receiving, from the microphone, information related to measured noise;
         identifying a type of the measured noise;
         determining, based on the information related to the measured noise and the identified type of the measured noise, an audible alert that will not be masked by the measured noise when the audible alert is produced by the alert module; and
         providing, to the alert module, instructions for producing the audible alert.

18. A computer-readable storage device storing a computer program including instructions for causing a computer to:
   receive, from a microphone of a dialysis machine, information related to measured noise;
   identify a type of the measured noise;
   determine, based on the information related to the measured noise and the identified type of the measured noise, an audible alert related to an operating condition of the dialysis machine, the audible alert determined such that the audible alert will not be masked by the measured noise when the audible alert is produced by an alert module of the dialysis machine; and
   provide, to the alert module, instructions for producing the audible alert.

* * * * *